(12) United States Patent
Biemans et al.

(10) Patent No.: US 8,753,645 B2
(45) Date of Patent: Jun. 17, 2014

(54) CONJUGATION PROCESS OF BACTERIAL POLYSACCHARIDES TO CARRIER PROTEINS

(75) Inventors: Ralph Leon Biemans, Rixensart (BE); Pierre Duvivier, Rixensart (BE); Ollivier Francis Nicolas Gavard, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

(21) Appl. No.: 13/581,824

(22) PCT Filed: Mar. 7, 2011

(86) PCT No.: PCT/EP2011/053400
§ 371 (c)(1),
(2), (4) Date: Aug. 30, 2012

(87) PCT Pub. No.: WO2011/110531
PCT Pub. Date: Sep. 15, 2011

(65) Prior Publication Data
US 2012/0321660 A1    Dec. 20, 2012

(30) Foreign Application Priority Data

Mar. 9, 2010 (GB) .................................. 1003922.0

(51) Int. Cl.
*A61K 39/385* (2006.01)
*C07K 1/08* (2006.01)
*C07K 1/113* (2006.01)

(52) U.S. Cl.
USPC .................. 424/197.11; 424/194.1; 530/402; 530/395

(58) Field of Classification Search
CPC combination set(s) only.
See application file for complete search history.

(56) References Cited

U.S. PATENT DOCUMENTS

| 4,356,170 | A | 10/1982 | Jennings et al. | |
| 7,955,605 | B2 * | 6/2011 | Prasad | ........................ 424/244.1 |
| 2007/0184071 | A1 | 8/2007 | Hausdorff et al. | |
| 2007/0184072 | A1 * | 8/2007 | Hausdorff et al. | ......... 424/244.1 |

FOREIGN PATENT DOCUMENTS

| WO | 2006/082530 | 8/2006 |
| WO | 2007/000322 | 1/2007 |

OTHER PUBLICATIONS

International Preliminary Report on Patentability mailed Dec. 20, 2012 for priority document International Application No. PCT/EP2011/053400 with Authorized Representative's response to the Written Opinion and the amended claims.
Anderson, et al., Vaccines Consisting of Periodate-Cleaved Oligosaccharides from the Capsule of *Haemophilus influenzae* Type b Coupled to a Protein Carrier: Structural and Temporal Requirements for Priming in the Human Infant, J Immunol 137(4): 1181-1186 (1986).
Steinhoff, et al., A randomized comparison of three bivalent *Streptococcus pneumoniae* glycoprotein conjugate vaccines in young children: effect of polysaccharide size and linkage characteristics, Pediatric Infect Dis J 13(5): 368-372 (1994).
Kim, et al., Monitoring activation sites on polysaccharides by GC-MS, Analytical Biochemistry 358(1): 136-142 (2006).

* cited by examiner

*Primary Examiner* — Padma V Baskar
(74) *Attorney, Agent, or Firm* — Alice P. Bradney

(57) ABSTRACT

Process for conjugation of bacterial saccharides including *Streptococcus pneumoniae* and *Haemophilus influenzae* saccharides by reductive amination are provided herein.

11 Claims, 4 Drawing Sheets

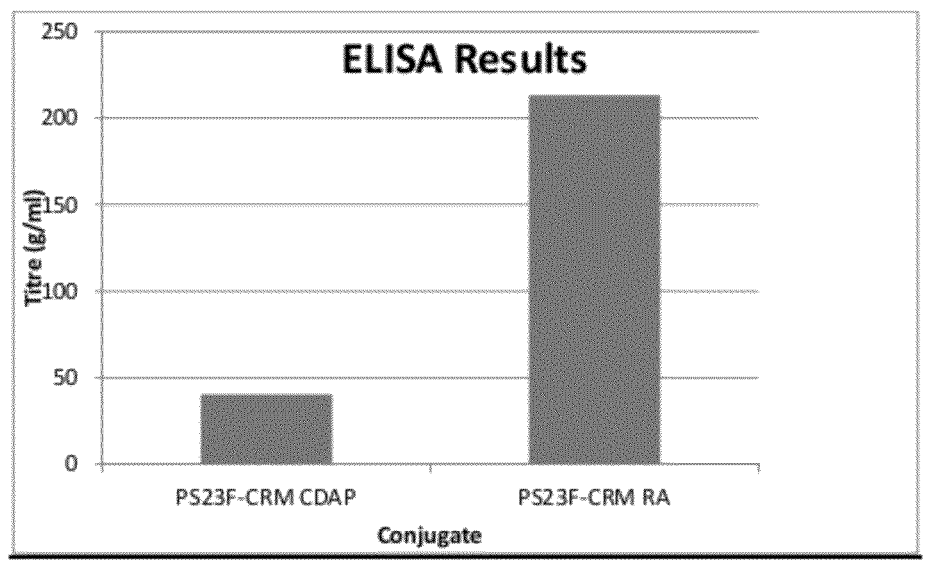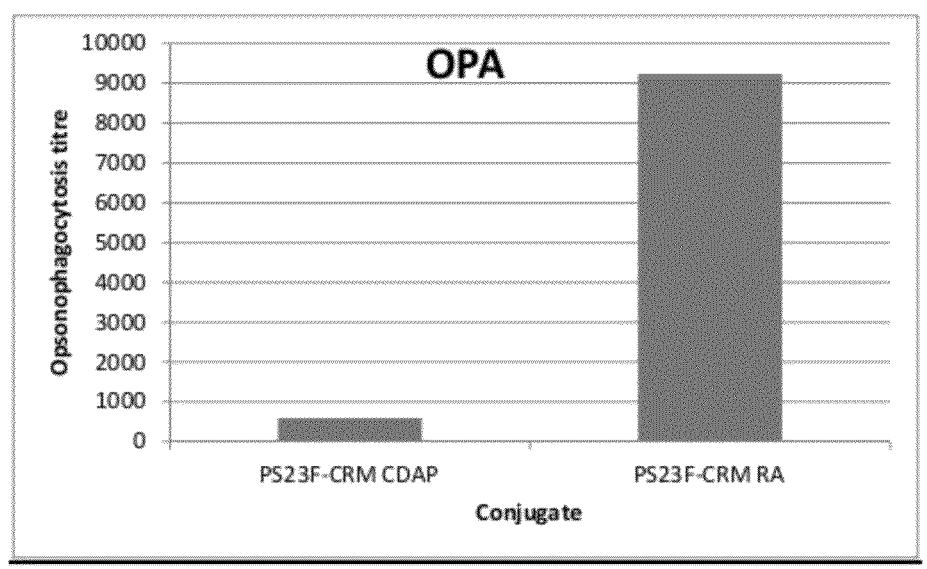
Figure 2

CONJUGATION PROCESS OF BACTERIAL POLYSACCHARIDES TO CARRIER PROTEINS

This application is filed pursuant to 35 U.S.C. §371 as a United States National Phase Application of International Patent Application Serial No. PCT/EP2011/053400 filed Mar. 7, 2011, which claims priority to United Kingdom Application No. 1003922.0 filed Mar. 9, 2010, the contents of each of the foregoing applications are hereby incorporated by reference.

Description

The present invention relates to a process for conjugation. In particular, it relates to the conjugation of saccharides and proteins using reductive amination.

BACKGROUND

Bacterial capsular polysaccharides have been widely used in immunology for many years for the prevention of bacterial disease. A problem with such a use, however, is the T-independent nature of the immune response. These antigens are thus poorly immunogenic in young children. This problem has been overcome through conjugating the polysaccharide antigens to a carrier protein (a source of T-helper epitopes) which may then be used to elicit a T-dependent immune response, even in the first year of life.

Various conjugation techniques are known in the art. Conjugates can be prepared by direct reductive amination methods as described in, US200710184072 (Hausdorff) U.S. Pat. No. 4,365,170 (Jennings) and U.S. Pat. No. 4,673,574 (Anderson). Other methods are described in EP-0-161-188, EP-208375 and EP-0-477508. The conjugation method may alternatively rely on activation of hydroxyl groups of the saccharide with 1-cyano-4-dimethylamino pyridinium tetrafluoroborate (CDAP) to form a cyanate ester. Such conjugates are described in PCT published application WO 93/15760 Uniformed Services University and WO 95/08348 and WO 96/29094. See also Chu C. et al Infect. Immunity, 1983 245 256.

Reductive amination involves two steps, (1) oxidation of the antigen, (2) reduction of the antigen and a carrier protein to form a conjugate. The oxidation step may involve reaction with periodate, however oxidation by periodate may lead to size reduction (WO94/05325).

SUMMARY OF INVENTION

The inventors have surprisingly found that using lower concentrations of periodate in the presence of low phosphate may lead to retention of size and/or the retention of epitopes.

In a first aspect of the invention there is provided a process for conjugating a bacterial saccharide(s) comprising the steps of
a) reacting the bacterial saccharide with 0.001-0.7, 0.005-0.5, 0.01-0.5, 0.1-1.2, 0.1-0.5, 0.1-0.2, 0.5-0.8, 0.1-0.8, 0.3-1.0 or 0.4-0.9 molar equivalents of periodate to form an activated bacterial saccharide;
b) mixing the activated bacterial saccharide with a carrier protein;
c) reacting the activated bacterial saccharide and the carrier protein with a reducing agent to form a conjugate;
or
a) reacting the bacterial saccharide with 0.001-0.7, 0.005-0.5, 0.01-0.5, 0.1-1.2, 0.1-0.5, 0.1-0.2, 0.5-0.8, 0.1-0.8, 0.3-1.0 or 0.4-0.9 molar equivalents of periodate to form an activated bacterial saccharide;
b) mixing the activated bacterial saccharide with a linker;
c') reacting the activated bacterial saccharide with the linker using a reducing agent to form a bacterial saccharide-linker;
d) reacting the bacterial saccharide-linker with a carrier protein to form a conjugate;
wherein step a) occurs in a buffer which does not contain an amine group, and the buffer has a concentration between 1-100 mM.

In a second aspect of the invention there is provided a conjugate obtainable by the process of the invention.

In a third aspect of the invention there is provided a conjugate obtained by the process of the invention.

In a fourth aspect of the invention there is provided an immunogenic composition comprising the conjugate of the invention and a pharmaceutically acceptable excipient.

In a fifth aspect of the invention there is provided a vaccine comprising the immunogenic composition of the invention.

In a sixth aspect of the invention there is provided a use of the immunogenic composition of the invention or the vaccine of the invention in the prevention or treatment of bacterial disease In a seventh aspect of the invention there is provided a use of the immunogenic composition of the invention or the vaccine of the invention in the preparation of a medicament for the prevention or treatment of bacterial disease.

In a eighth aspect of the invention there is provided a method of preventing or treating bacterial infection comprising administration of the immunogenic composition of the invention or the vaccine of the invention to a patient.

In an ninth aspect of the invention there is provided an activated bacterial saccharide, wherein the activated bacterial saccharide comprises a repeat unit of formula (I):

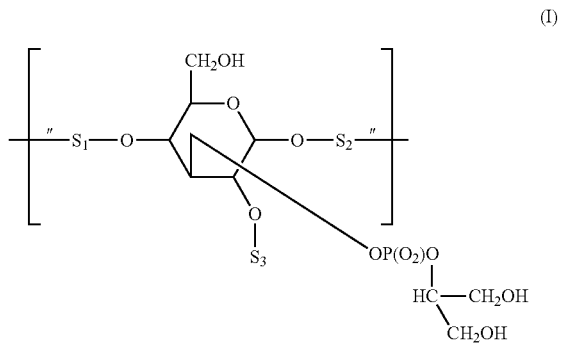

wherein the activated bacterial saccharide comprises n repeat units and n is between 2 and 2400, between 500 and 2000, between 750 and 1500, between 1000 and 2000 or between 1500 and 2300.

wherein at least 0.001%, 0.01%, 0.1%, 0.5%, 1%, 2%, 5%, 10% or 30% but less than 0.001%, 0.01%, 0.1%, 0.5%, 1%, 2%, 5%, 10%, 30% or 50% of S1 is

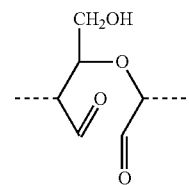

and the remainder is

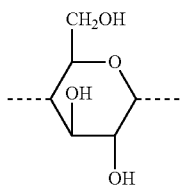

wherein S2 is either

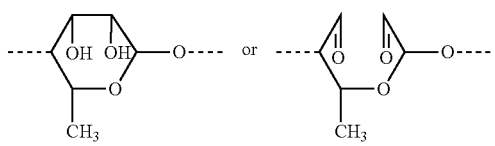

and wherein S3 is either

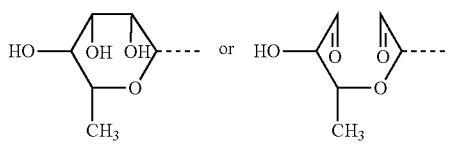

DESCRIPTION OF FIGURES

FIG. 2. Comparison of immunogenicity of 23F conjugates using either CDAP or reductive amination conjugation. Graph a) describes the results of an ELISA assay. Graph b) describes the results of an opsonophagocytosis assay.

DETAILED DESCRIPTION OF THE INVENTION

Figure 1:
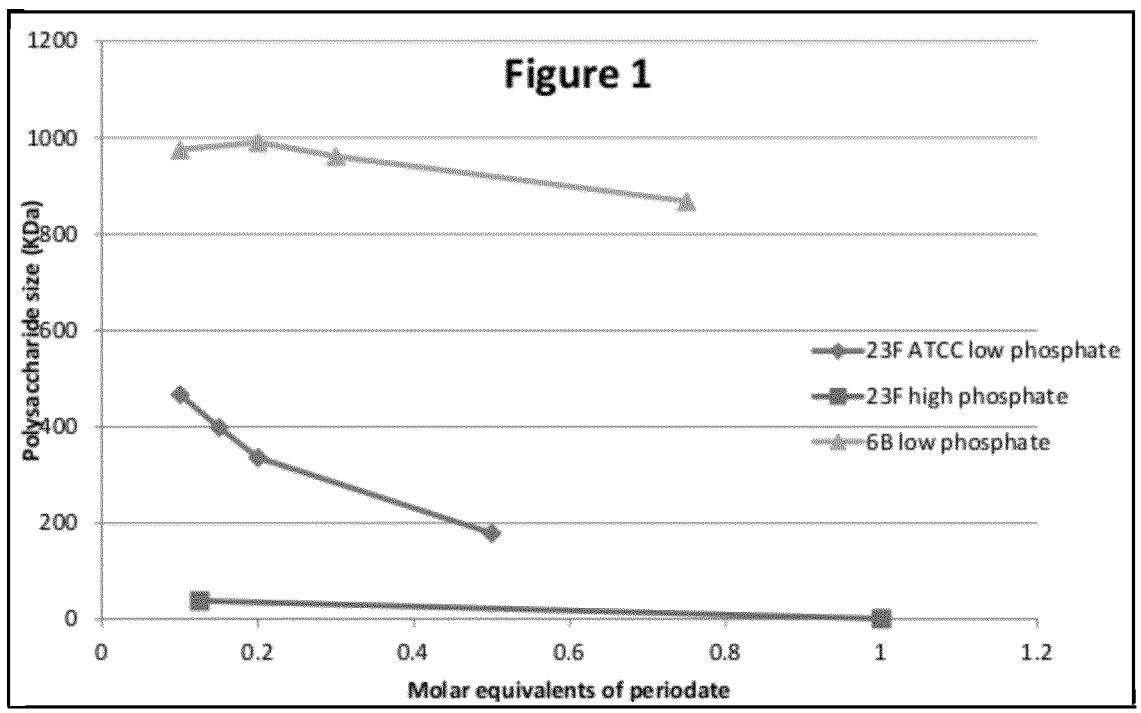
FIG. 1. Size of 23F and 6B polysaccharides following periodate treatment. The line marked with triangles shows the size of 6B in 10 mM phosphate buffer, the line marked with diamonds shows the size of 23F in 10 mM phosphate buffer and the line marked with squares shows the size of 23F in 100 mM phosphate buffer.

The invention relates to an improved process for conjugating an antigen to a carrier protein. In particular, the invention provides a process for conjugating a bacterial saccharide(s) comprising the steps of
  a) reacting the bacterial saccharide with 0.001-0.7, 0.005-0.5, 0.01-0.5, 0.1-1.2, 0.1-0.5, 0.1-0.2, 0.5-0.8, 0.1-0.8, 0.3-1.0 or 0.4-0.9 molar equivalents of periodate to form an activated bacterial saccharide;
  b) mixing the activated bacterial saccharide with a carrier protein;
  c) reacting the activated bacterial saccharide and the carrier protein with a reducing agent to form a conjugate;
or
  a) reacting the bacterial saccharide with 0.001-0.7, 0.005-0.5, 0.01-0.5, 0.1-1.2, 0.1-0.5, 0.1-0.2, 0.5-0.8, 0.1-0.8, 0.3-1.0 or 0.4-0.9 molar equivalents of periodate to form an activated bacterial saccharide;
  b) mixing the activated bacterial saccharide with a linker;
  c') reacting the activated bacterial saccharide with the linker using a reducing agent to form a bacterial saccharide-linker;
  d) reacting the bacterial saccharide-linker with a carrier protein to form a conjugate;
wherein step a) occurs in a buffer which does not contain an amine group, and the buffer has a concentration between 1-100 mM.

The term 'periodate' includes both periodate and periodic acid. This term also includes both metaperiodate ($IO_4^-$) and orthoperiodate ($IO_6^{5-}$), however in one particular embodiment the periodate used in the method of the invention is metaperiodate. The term 'periodate' also includes the various salts of periodate including sodium periodate and potassium periodate. In one embodiment the periodate used is sodium metaperiodate. When an antigen reacts with periodate, periodate oxidises vicinal hydroxyl groups to form carbonyl or aldehyde groups and causes cleavage of a C—C bond. For this reason the term 'reacting an antigen with periodate' includes oxidation of vicinal hydroxyl groups by periodate.

For the purposes of the invention an 'activated bacterial saccharide' is a bacterial saccharide which has been activated by step a) of the process of the invention.

For the purposes of the invention the term 'conjugate' indicates a bacterial saccharide linked covalently to a carrier protein. In one embodiment a bacterial saccharide is linked directly to a carrier protein. In a second embodiment a bacterial saccharide is linked to a protein through a spacer/linker.

The buffer used in step a) is a buffer which does not contain an amine group. In one embodiment the buffer is selected from the list consisting of phosphate buffer, borate buffer, acetate buffer, carbonate buffer, maleate buffer and citrate buffer. In a second embodiment the buffer is an inorganic buffer. The term inorganic buffer includes any buffer solution wherein the buffering capacity is due to the presence of a compound which does not contain carbon. Inorganic buffers of the invention include phosphate buffer and borate buffer. In one embodiment the buffer is phosphate buffer.

In one embodiment the buffer has a concentration between 1-100 mM, 5-80 mM, 1-50 mM, 1-25 mM, 10-40 mM, 1-10 mM, 5-15 mM, 8-12 mM, 10-20 mM, 5-20 mM, 10-50 mM, around 10 mM or around 20 mM. In a further embodiment the pH in step a) is pH 2.5-8.0, pH 5.0-7.0, pH 5.5-6.5, pH 5.8-6.3, or around pH 6.0.

The term "saccharide" throughout this specification may indicate polysaccharide, techoic acid or oligosaccharide and includes all three. It may indicate lipopolysaccharide (LPS) or lipooliogosaccharide (LOS). Before use Polysaccharides may be isolated from a source strain or isolated from the source strain and sized to some degree by known methods (see for example EP497524 and EP497525; Shousun Chen Szu et al.—Carbohydrate Research Vol 152 p 7-20 (1986)) for instance by microfluidisation. Oligosaccharides have a low number of repeat units (typically 5-30 repeat units) and are typically hydrolysed polysaccharides.

In one embodiment the bacterial saccharide is a bacterial capsular saccharide. In one embodiment of the present invention the bacterial saccharide originates from Group B *Streptococcus*, *Vibrio cholera*, *Streptococus pneumoniae* (*S. pneumoniae*), *Haemophilus influenzae* (*H. influenzae*), *Neisseria meningitidis* (*N. meningitidis*), *Staphylococcus aureus* (*S. aureus*), enterococci, *Salmonella* Vi, or *Staphylococcus epidermidis* (*S. epidermidis*). In a further embodiment the bacterial saccharide originates from *S. pneumoniae*, *H. influen-* zae, N. meningitidis, S. aureus, enterococci, Salmonella Vi, or S. epidermidis. In a yet further embodiment the bacterial saccharide is a bacterial capsular saccharide selected from a list consisting of: N. meningitidis serogroup A (MenA), B (MenB), C (MenC), W135 (MenW) or Y (MenY), Group B Streptococcus group Ia, Ib, II, III, IV, V, VI, or VII, Staphylococcus aureus type 5, Staphylococcus aureus type 8, Salmonella typhi (Vi saccharide), Vibrio cholerae, or H. influenzae type b. In one embodiment the bacterial saccharide is a capsular saccharide from Streptococcus pneumoniae serotypes 1, 2, 3, 4, 5, 6A, 6B, 7F, 8, 9N, 9V, 10A, 11A, 12F, 14, 15B, 17F, 18C, 19A, 19F, 20, 22F, 23F or 33F. In a further embodiment the bacterial saccharide is an S. pneumoniae capsular saccharide selected from the group consisting of 5, 6B, 6A, 7F, 9V, 14, or 23F. Optionally the bacterial saccharide of the invention is an S. pneumoniae capsular saccharide 23F, 6B or 6A. In one embodiment the bacterial saccharide is an S. pneumoniae capsular saccharide 23F. In one embodiment the bacterial saccharide is an S. pneumoniae capsular saccharide 6B. In one embodiment the bacterial saccharide is an S. pneumoniae capsular saccharide 6A. In a yet further embodiment the bacterial saccharide is Haemophilus influenzae b (Hib) polysaccharide or oligosaccharide. In one embodiment the bacterial saccharide contains vicinal anti diols.

The bacterial saccharide may be either a native polysaccharide or may have been reduced in size by a factor of no more than x2, x4, x6, x8, x10 or x20 (for instance by microfluidization [e.g. by Emulsiflex C-50 apparatus] or other known technique [for instance heat, chemical, oxidation, sonication methods]). In one embodiment the bacterial saccharide is microfluidised before step a). Oligosaccharides may have been reduced in size substantially further [for instance by known heat, chemical, or oxidation methods].

For the purposes of the invention, "native polysaccharide" refers to a bacterial saccharide that has not been subjected to a process, the purpose of which is to reduce the size of the saccharide. A polysaccharide can become slightly reduced in size during normal purification procedures. Such a saccharide is still native. Only if the polysaccharide has been subjected to techniques which reduce a saccharide in size would the polysaccharide not be considered native.

The weight-average molecular weight of a bacterial saccharide suitable for conjugation by the process of the invention may be between 20 kDa and 2000 kDa, between 30 kDa and 1000 kDa, between 40 kDa and 500 kDa, between 50 kDa and 400 kDa, between 75 kDa and 300 kDa or between 1000 kDa and 2000 kDa. In the case of the native 23F capsular saccharide from S. pneumoniae, the average molecular weight of the native polysaccharide is between 750-1500 kDa or 1200-1300 kDa. In the case of the native Hib saccharide, the average molecular weight of the native polysaccharide is between 100 and 250 kDa. The molecular weight or average molecular weight of a saccharide herein refers to the weight-average molecular weight (Mw) of the bacterial saccharide measured prior to conjugation and is measured by MALLS. The MALLS technique is well known in the art. For MALLS analysis of saccharides, two columns (TSKG6000 and 5000PWxl) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm). MALLS analyses may be carried out using a TSKGMPwxI and 50 mM Na/K PO4, 200 mM NaCl pH 7.0 as elution buffer with 0.75 ml/min using RI/DAWN-EOS detector. In an embodiment, the polydispersity of the saccharide is 1-1.5, 1-1.3, 1-1.2, 1-1.1 or 1-1.05 and after conjugation to a carrier protein, the polydispersity of the conjugate is 1.0-2.5, 1.0-2.0. 1.0-1.5, 1.0-1.2, 1.5-2.5, 1.7-2.2 or 1.5-2.0. All polydispersity measurements are generated by MALLS.

Treatment with periodate may lead to a reduction in the size of the bacterial saccharide (sizing effect). In one embodiment the process of the invention reduces this sizing effect. This is seen for the 23F bacterial saccharide from Streptococcus pneumoniae (as in example 1). For this reason, in one embodiment the average molecular weight of a bacterial saccharide of the invention is between 1-1100 kDa, 100-470 kDa, 200-300 kDa, 600-1100 kDa or 800-1000 kDa after step a) (measured by MALLS as described above). In one embodiment the average molecular weight of the 23F saccharide is between 100-470 kDa or 200-300 kDa after step a). In one embodiment the average molecular weight of the Hib bacterial saccharide is between 1 and 50 kDa or between 5 and 10 kDa after step a).

The term "carrier protein" is intended to cover both small peptides and large polypeptides (>10 kDa). The carrier protein may be any peptide or protein. It may comprise one or more T-helper epitopes. The carrier protein may be tetanus toxoid (TT), tetanus toxoid fragment C, non-toxic mutants of tetanus toxin [note all such variants of TT are considered to be the same type of carrier protein for the purposes of this invention], polypeptides comprising tetanus toxin T-cell epitopes such as N19 (WO2006/067632), diphtheria toxoid (DT), CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. Nos. 4,709,017 or 4,950,740; mutation of at least one or more residues Lys 516, Lys 526, Phe 530 and/or Lys 534 and other mutations disclosed in U.S. Pat. Nos. 5,917,017 or 6,455,673; or fragment disclosed in U.S. Pat. No. 5,843,711] (note all such variants of DT are considered to be the same type of carrier protein for the purposes of this invention), pneumococcal pneumolysin (Kuo et al (1995) Infect Immun 63; 2706-13), OMPC (meningococcal outer membrane protein—usually extracted from N. meningitidis serogroup B—EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of C. difficile (WO 00/61761), H. influenzae Protein D (EP594610 and WO 00/56360), pneumococcal PhtA (WO 98/18930, also referred to Sp36), pneumococcal PhtD (disclosed in WO 00/37105, and is also referred to Sp036D), pneumococcal PhtB (disclosed in WO 00/37105, and is also referred to Sp036B), or PhtE (disclosed in WO00/30299 and is referred to as BVH-3).

In one embodiment of the invention the carrier protein is selected from the group consisting of: tetanus toxoid (TT), fragment C of tetanus toxoid, diphtheria toxoid (DT), CRM197, Pneumolysin (Ply), protein D, PhtD, PhtDE and N19. In a further embodiment the carrier protein is CRM197. In a still further embodiment the carrier protein is tetanus toxoid (TT).

In one embodiment step a) is carried out in the dark.

When an antigen reacts with periodate, periodate oxidises vicinal hydroxyl groups to form carbonyl or aldehyde groups and causes cleavage of a C—C bond. The oxidation step (step a)) may occur as described below:

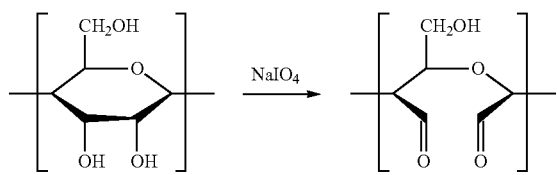

When low concentrations of buffer, in particular phosphate buffer and low amounts of periodate are used, this may reduce the sizing effect described above.

*Streptococcus pneumoniae* capsular saccharides contain vicinal hydroxyl groups which are capable of being oxidised by periodate as can be seen from the structures of the repeated regions shown below:

PS1

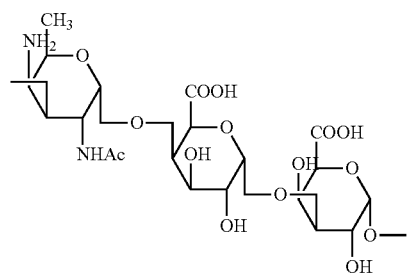

PS4

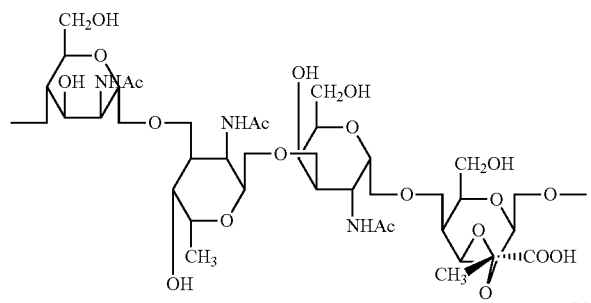

PS5

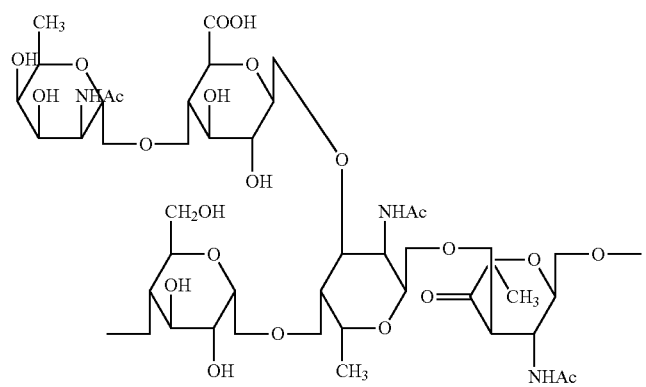

PS 6A

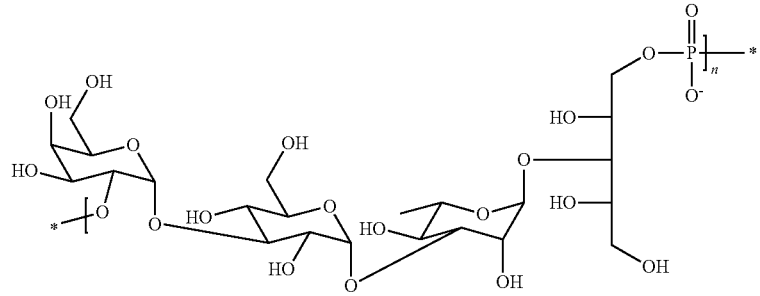

PS 6B

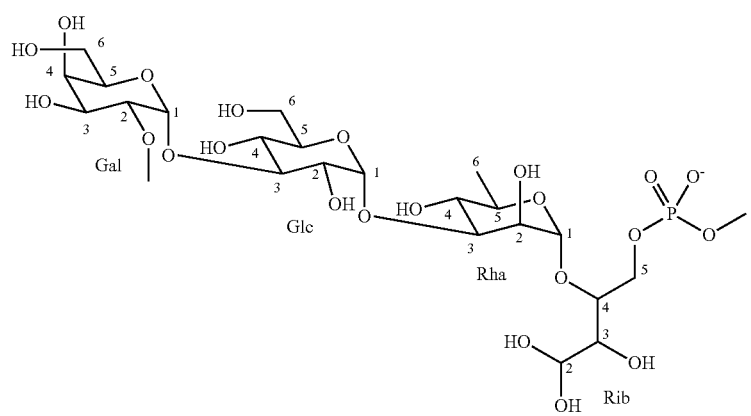

-continued
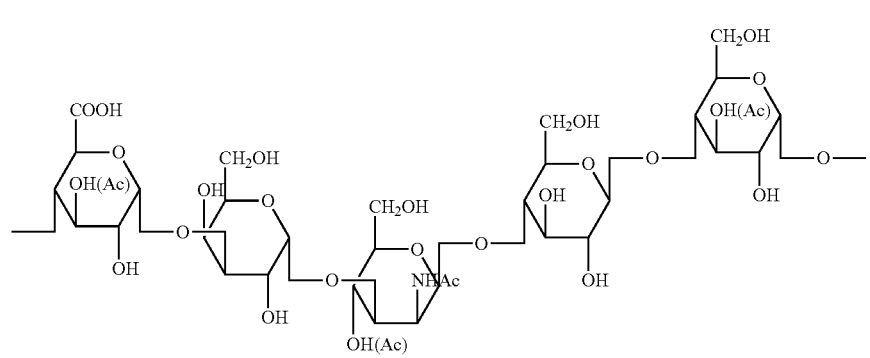
PS9
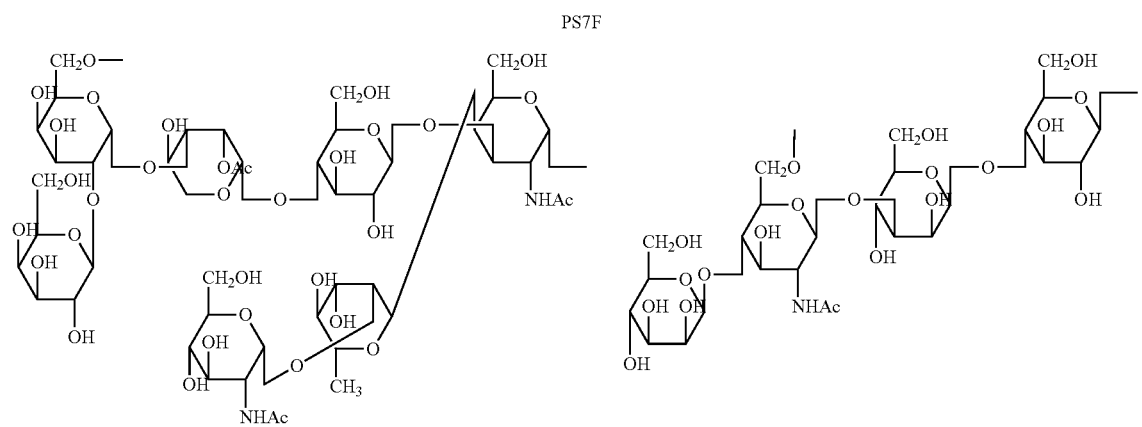
PS7F
PS14
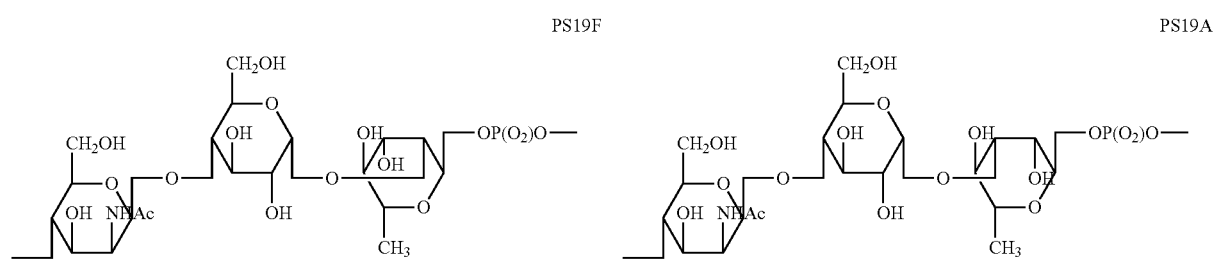
PS19F
PS19A
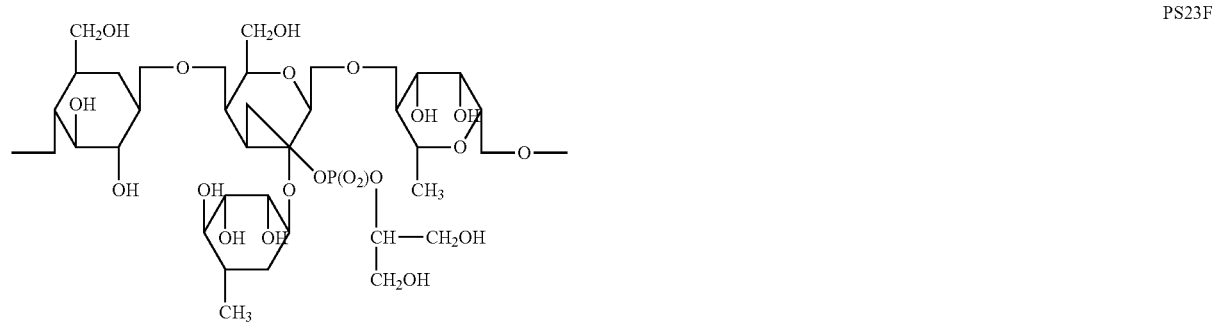
PS23F

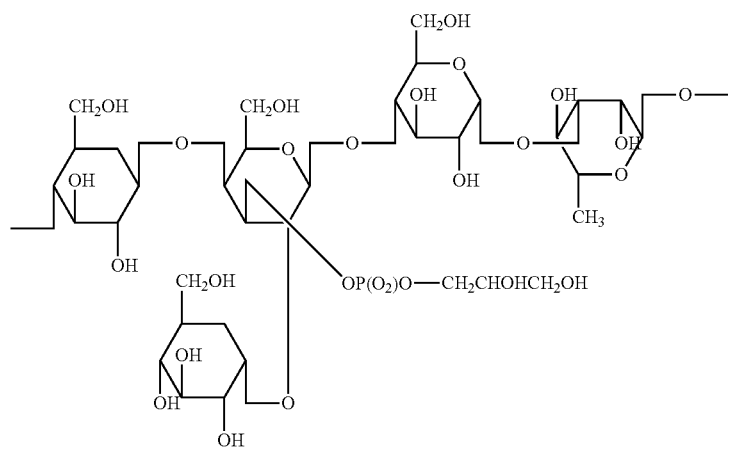

PS18C

In one embodiment less than 0.001%, 0.01%, 0.1%, 0.5%, 1%, 2%, 5%, 10%, 30% or 50% of the vicinal diols of the bacterial saccharide become oxidised during step a).

In one embodiment the carbonyl group produced in step a) reacts with an amine group on the carrier protein in step c). This may occur according to the following reaction scheme:

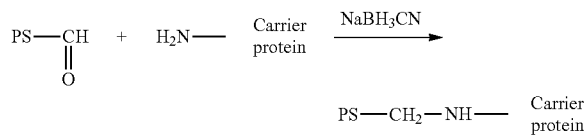

In one embodiment the bacterial saccharide is present at a concentration of between 0.2 g/l and 14 g/l 8 g/l and 12 g/l, 10 g/l and 12 g/l, 1 g/l and 4 g/l, 0.2 g/l and 1 g/l or between 0.4 g/l and 0.6 g/l or around 11 g/l or around 0.5 g/l in step a). In one embodiment the initial concentration of carrier protein in step b) is between 0.5 g/l and 35 g/l, 25 g/l and 35 g/l, 0.5 g/l and 5 g/l or between 0.8 g/l and 2 g/l or around 32 g/l or 1 g/l. In a further embodiment the initial concentration of activated bacterial saccharide in step b) is between 0.2 g/l and 20 g/l, 10 g/l and 28 g/l, or 0.2 g/l and 4 g/l or between 1 g/l and 2 g/l or around 15 g/l or 1.6 g/l. In a further embodiment the initial ratio of activated bacterial saccharide to carrier protein in step b) is 2.0:1 to 0.1:1, 1.8:1 to 0.4:1, 1.4:1 to 1.6:1, 1:1 to 1.4:1, 1.8:1 to 1.6:1, 0.8:1 to 0.4:1, 0.7:1 to 0.5:1, or 0.7:1 to 0.6:1 (w/w). In a further embodiment the final ratio of carrier protein to bacterial saccharide after step c) or c') is 0.5:1 to 4:1, 0.8:1 to 3.2:1, 0.5:1 to 1.8:1, 1.4:1 to 1.8:1, 1:1 to 1.2:1 or 2.5:1 to 3.5:1.

In one embodiment the temperature of the reaction in step a) is 4-40° C., 10-32° C., 17-30° C. or 22-27° C. Typically this temperature is maintained through step a). The reaction temperature during step c) is 4-40° C., 10-32° C., 17-30° C. or 22-27° C. Typically this temperature is maintained through step c).

In one embodiment step a) of the process of the invention takes place in less than 30 hours, between 5 and 25 hours, between 15 and 25 hours, between 30 minutes and 25 hours, between 1 hour and 35 hours, between 10 and 20 hours, or between 15 and 20 hours around 18 hours or around 1 hour. In one embodiment step c) of the process of the invention takes place in between 10-60 hours, 10-20 hours, 20-60 hours, between 30-50 hours, or between 35-45 hours.

Conjugation may also occur through the addition of a hetero- or homo-bifunctional linker using the chemistry of the invention. One end of the linker will react with the activated antigen by reductive amination, however the other end of the linker may react with the carrier protein using any type of chemistry. For this reason the linker will contain at least one reactive amino group, if the linker is homo-bifunctional it will contain two reactive amino groups, if the linker is heterobifunctional it will contain one reactive amino group and a different reactive group, in one embodiment this second reactive group is a reactive carbonyl group. In one embodiment the linker is between 1 and 20 Angstroms in length. In a further embodiment the linker has between 4 and 20, 4 and 12, or 5 and 10 carbon atoms. A possible linker is adipic acid dihydrazide (ADH). Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. Nos. 4,673,574, 4,808,700), hexane diamine and 6-aminocaproic acid (U.S. Pat. No. 4,459,286).

In general the following types of chemical groups on the carrier protein can be used for coupling/conjugation as the second reactive group:

A) Carboxyl (for instance via aspartic acid or glutamic acid). In one embodiment this group is linked to an amino group on a linker with carbodiimide chemistry e.g. with EDAC (1-Ethyl-3-(3-dimethylaminopropyl)carbodiimide)).
Note: instead of EDAC above, any suitable carbodiimide may be used.

B) Amino group (for instance via lysine). In one embodiment this group is linked to a carboxyl group on a linker with carbodiimide chemistry e.g. with EDAC. In another embodiment this group is linked to hydroxyl groups activated with CDAP or CNBr on a linker; to linkers having an aldehyde group; to linkers having a succinimide ester group.

C) Sulphydryl (for instance via cysteine). In one embodiment this group is linked to a bromo or chloro acetylated linker with maleimide chemistry. In one embodiment this group is activated/modified with bis diazobenzidine.

D) The protein could be modified to contain an alkynyl or azide group, this could be conjugated to the linker using the 'click' chemistry (described in Tetrahedron letters (June 2005) 46:4479-4482).
Note: instead of EDAC above, any suitable carbodiimide may be used.

Reducing agents which are suitable for use in the process of the invention include the cyanoborohydrides, such as sodium cyanoborohydride, borane-pyridine, or borohydride exchange resin. In one embodiment the reducing agent is sodium cyanoborohydride. In one embodiment between 0.5 and 2, 0.6 and 1.5 or 0.8 and 1.2 or around 1.0 molar equivalent of sodium cyanoborohydride is used in step c). In a further embodiment the reducing agent comprises sodium triacetoxyborohydride, in a further embodiment between 2 and 10 or between 3 and 9 molar equivalent or around 2.5 molar equivalent of sodium triacetoxyborohydride is used in step c).

Before step c) the activated bacterial saccharide and the carrier protein may be lyophilised. In one embodiment the activated bacterial saccharide and the carrier protein are lyophilised together. This can occur before step b), or after step b). In one embodiment the lyophilisation takes place in the presence of a non-reducing sugar, possible non-reducing sugars include sucrose, trehalose, raffinose, stachyose, melezitose, dextran, mannitol, lactitol and palatinit.

In a further embodiment the non-reducing sugar is selected from the group consisting of sucrose, trehalose or mannitol.

In one embodiment steps b) and/or c) are carried out in DMSO (dimethylsulfoxide) solvent. In a further embodiment steps b) and/or c) are carried out in DMF (dimethylformamide) solvent. The DMSO or DMF solvent may be used to reconstitute the activated bacterial saccharide and carrier protein which has been lyophilised.

At the end of step c) there may be unreacted carbonyl groups remaining in the conjugates, these may be capped using a suitable capping agent. In one embodiment this capping agent is sodium borohydride ($NaBH_4$), for example the product of step c) may be reacted with sodium borohydride for 15 mins-15 hrs, 15 mins-45 mins, 2-10 hrs or 3-5 hrs, around 30 mins or around 4 hrs. In a further embodiment capping is achieved by mixing the product of step c) with around 2 molar equivalents or between 1.5 and 10 molar equivalents of $NaBH_4$.

The invention also provides a further step e) of purifying the conjugate, step e) may comprise diafiltration, for example diafiltration with a cut-off of 100 kDa. In addition or alternatively step e) may comprise ion exchange chromatography. In a further embodiment step e) may comprise size exclusion chromatography. In one embodiment the process of claims 1-51 comprises a further step f), wherein the conjugate is sterile filtered.

The conjugate may also be mixed with further antigens. In one embodiment the further antigens comprise at least 7, 8, 9, 10, 11, 12, 13, 14, 15, 16, 17, 18, 19 or 20 *S. pneumoniae* saccharides selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. In one embodiment the further antigens comprise *S. pneumoniae* saccharides 4, 6B, 9V, 14, 18C, 19F and 23F. In one embodiment the further antigens comprise *S. pneumoniae* saccharides 4, 6B, 9V, 14, 18C and 19F. In one embodiment the further antigens comprise *S. pneumoniae* saccharides 4, 9V, 14, 18C, 19F and 23F. In one embodiment the further antigens comprise *S. pneumoniae* saccharides 1, 4, 5, 6B, 7F, 9V, 14, 18C, 19F and 23F. In one embodiment the further antigens comprise *S. pneumoniae* saccharides 1, 4, 5, 6B, 7F, 9V, 14, 18C, and 19F. In one embodiment the further antigens comprise *S. pneumoniae* saccharides 1, 4, 5, 7F, 9V, 14, 18C, 19F and 23F. In one embodiment the further antigens comprise *S. pneumoniae* saccharides 1, 3, 4, 5, 6A, 6B, 7F, 9V, 14, 18C, 19A, 19F and 23F. In one embodiment the further antigens comprise *S. pneumoniae* saccharides 1, 3, 4, 5, 6A, 6B, 7F, 9V, 14, 18C, 19A and 19F. In one embodiment the further antigens comprise *S. pneumoniae* saccharides 1, 3, 4, 5, 6A, 7F, 9V, 14, 18C, 19A, 19F and 23F. In one embodiment the further antigens comprise *S. pneumoniae* saccharides 1, 4, 5, 6A, 6B, 7F, 9V, 14, 18C, 19A, 19F and 23F. In one embodiment the further antigens comprise *S. pneumoniae* saccharides 1, 4, 5, 6A, 6B, 7F, 9V, 14, 18C, 19A and 19F. In one embodiment the further antigens comprise *S. pneumoniae* saccharides 1, 4, 5, 6A, 7F, 9V, 14, 18C, 19A, 19F and 23F.

Any of the saccharides listed as 'further antigens' are optionally conjugated to a carrier protein either by the process of the invention or by a different process. Optionally these further antigens are conjugated to the carrier proteins listed above.

In an embodiment, the further antigens comprise *S. pneumoniae* capsular saccharide 1 conjugated to protein D or CRM197. In an embodiment, the further antigens comprise *S. pneumoniae* capsular saccharide 3 conjugated to protein D, CRM197, pneumolysin or PhtD or fragment or fusion protein thereof. In an embodiment, the further antigens comprise *S. pneumoniae* capsular saccharide 4 conjugated to protein D or CRM197. In an embodiment, the further antigens comprise *S. pneumoniae* capsular saccharide 5 conjugated to protein D or CRM197. In an embodiment, the further antigens comprise *S. pneumoniae* capsular saccharide 6B conjugated to protein D or CRM197. In an embodiment, the further antigens comprise *S. pneumoniae* capsular saccharide 7F conjugated to protein D or CRM197. In an embodiment, the further antigens comprise *S. pneumoniae* capsular saccharide 9V conjugated to protein D or CRM197. In an embodiment, the further antigens comprise *S. pneumoniae* capsular saccharide 14 conjugated to protein D or CRM197. In an embodiment, the further antigens comprise *S. pneumoniae* capsular saccharide 23F conjugated to protein D or CRM197. In an embodiment, the further antigens comprise *S. pneumoniae* capsular saccharide 18C conjugated to tetanus toxoid or CRM197. In an embodiment, the further antigens comprise *S. pneumoniae* capsular saccharide 19A conjugated to pneumolysin or CRM197. In an embodiment, the further antigens comprise *S. pneumoniae* capsular saccharide 22F conjugated to CRM197 or PhtD or fragment of fusion protein thereof. In an embodiment, the further antigens comprise *S. pneumoniae* capsular saccharide 6A conjugated to pneumolysin or a *H. influenzae* protein, optionally protein D or PhtD or fusion protein thereof or CRM197. In an embodiment, the further antigens comprise *S. pneumoniae* capsular saccharide 6C conjugated to pneumolysin or a *H. influenzae* protein, optionally protein D or PhtD or fusion protein thereof or CRM197. In an embodiment, the further antigens comprise *S. pneumoniae* capsular saccharide 19F conjugated to Diphtheria toxoid (DT).

The further antigens may also comprise *Streptococcus pneumoniae* proteins. In one embodiment the further antigens comprise at least 1 protein selected from the group consisting of the Poly Histidine Triad family (PhtX), Choline Binding protein family (CbpX), CbpX truncates, LytX family, LytX truncates, CbpX truncate-LytX truncate chimeric proteins (or fusions), pneumolysin (Ply), PspA, PsaA, Sp128, Sp101, Sp130, Sp125 and Sp133.

The further antigens may also comprise antigens from further bacterial species. In one embodiment the vaccine or immunogenic composition comprises antigens originating from *S. pneumoniae* (*S. pneumoniae*), *Haemophilus influenzae* (*H. Influenzae*), *Neisseria meningitidis* (*N. Meningitidis*), *Escherichia coli* (*E. col*)*i*, *Moraxella cattharlis* (*M. cattarhalis*), tetanus, diphtheria, pertussis, *Staphylococcus epidermidis* (*S. epidermidis*), enterococci, *Pseudomonas* or *Staphylococcus aureus* (*S. aureus*).

In one embodiment the further antigens comprise *M. cattarhalis* antigens, preferred *M. cattarhalis* antigens are: OMP106 [WO 97/41731 (Antex) & WO 96/34960 (PMC)]; OMP21; LbpA & LbpB [WO 98/55606 (PMC)]; TbpA & TbpB [WO 97/13785 & WO 97/32980 (PMC)]; CopB [Helminen M E, et al. (1993) Infect. Immun. 61:2003-2010]; UspA1/2 [WO 93/03761 (University of Texas)]; and OmpCD. Examples of non-typeable *Haemophilus influenzae* antigens which can be included in a combination vaccine (especially for the prevention of otitis media) include: Fimbrin protein [(U.S. Pat. No. 5,766,608—Ohio State Research Foundation)] and fusions comprising peptides therefrom [eg LB1(f) peptide fusions; U.S. Pat. No. 5,843,464 (OSU) or WO 99/64067]; OMP26 [WO 97/01638 (Cortecs)]; P6 [EP 281673 (State University of New York)]; TbpA and TbpB; Hia; Hmw-1,2; Hap; and D15.

In a further embodiment the further antigens comprise Diphtheria toxoid (DT), tetanus toxoid (TT), and pertussis components [typically detoxified Pertussis toxoid (PT) and filamentous haemagglutinin (FHA) with optional pertactin (PRN) and/or agglutinin 1+2], for example the marketed vaccine INFANRIX-DTPaTM (SmithKlineBeecham Biologicals) which contains DT, TT, PT, FHA and PRN antigens, or with a whole cell pertussis component for example as marketed by SmithKlineBeecham Biologicals s.a., as TritanrixTM. In a further embodiment the further antigens comprise Hepatitis B surface antigen (HepB).

In a further embodiment the further antigens comprise the PRP capsular saccharide of *H. influenzae* (Hib).

In a further embodiment the further antigens comprise at least one capsular saccharide from *N. meningitidis* A, C, W or Y. In a further embodiment the further antigens comprise at least one conjugate of a capsular saccharide from *N. meningitidis* A, C, W or Y.

The conjugate may also be mixed with an adjuvant. Suitable adjuvants include, but are not limited to, aluminium salts (aluminium phosphate or aluminium hydroxide), monophosphoryl lipid A (for example 3D-MPL), saponins (for example QS21), oil in water emulsions, blebs or outer membrane vesicle preparations from Gram negative bacterial strains (such as those taught by WO02/09746), lipid A or derivatives thereof, alkyl glucosamide phosphates or combinations of two or more of these adjuvants.

In a further embodiment the conjugate of the invention is mixed with a pharmaceutically acceptable excipient.

In a further aspect of the invention there is provided a conjugate obtainable by the process of the invention. In a further aspect of the invention there is provided a conjugate obtained by the process of the invention. The invention also provides an immunogenic composition comprising the conjugate of the invention and a pharmaceutically acceptable excipient. In one embodiment the pharmaceutical acceptable excipient does not contain a chloride salt, in a further embodiment the pharmaceutical excipient does not contain sodium chloride. In one embodiment the pharmaceutical excipient comprises a buffer selected from the group consisting of maleate, tris, or citrate. In a further embodiment the buffer is maleate buffer.

The immunogenic composition of the invention may comprise further antigens, in particular those described as 'further antigens' above. The immunogenic composition may comprise an adjuvant, particularly those described above.

The invention also provides a vaccine comprising the immunogenic composition of the invention.

The vaccine preparations containing immunogenic compositions of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is possible (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for optimal coordination of the immune responses with respect to each other). In addition to a single route of administration, 2 different routes of administration may be used. For example, saccharides or saccharide conjugates may be administered IM (or ID) and bacterial proteins may be administered IN (or ID). In addition, the vaccines of the invention may be administered IM for priming doses and IN for booster doses.

The content of protein antigens in the vaccine will typically be in the range 1-100 µg, optionally 5-50µg, most typically in the range 5-25µg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

Although the vaccines of the present invention may be administered by any route, administration of the described vaccines into the skin (ID) forms one embodiment of the present invention. Human skin comprises an outer "horny" cuticle, called the stratum corneum, which overlays the epidermis. Underneath this epidermis is a layer called the dermis, which in turn overlays the subcutaneous tissue. Researchers have shown that injection of a vaccine into the skin, and in particular the dermis, stimulates an immune response, which may also be associated with a number of additional advantages. Intradermal vaccination with the vaccines described herein forms an optional feature of the present invention.

The conventional technique of intradermal injection, the "mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

When the vaccines of the present invention are to be administered to the skin, or more specifically into the dermis, the vaccine is in a low liquid volume, particularly a volume of between about 0.05 ml and 0.2 ml.

The content of antigens in the skin or intradermal vaccines of the present invention may be similar to conventional doses as found in intramuscular vaccines (see above). However, it is a feature of skin or intradermal vaccines that the formulations may be "low dose". Accordingly the protein antigens in "low dose" vaccines are optionally present in as little as 0.1 to 10μg or 0.1 to 5 μg per dose; and the saccharide (optionally conjugated) antigens may be present in the range of 0.01-1μg, or between 0.01 to 0.5 μg of saccharide per dose.

As used herein, the term "intradermal delivery" means delivery of the vaccine to the region of the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

In one aspect of the invention is provided a vaccine kit, comprising a vial containing an immunogenic composition of the invention, optionally in lyophilised form, and further comprising a vial containing an adjuvant as described herein. It is envisioned that in this aspect of the invention, the adjuvant will be used to reconstitute the lyophilised immunogenic composition.

A further aspect of the invention is a method of immunising a human host against bacterial disease infection comprising administering to the host an immunoprotective dose of the immunogenic composition or vaccine or kit of the invention. A further aspect of the invention is a method of immunising a human host against infection caused by *S. pneumoniae* and/or *Haemophilus influenzae* comprising administering to the host an immunoprotective dose of the immunogenic composition or vaccine or kit of the invention.

A further aspect of the invention is an immunogenic composition of the invention for use in the treatment or prevention of bacterial disease. A further aspect of the invention is an immunogenic composition of the invention for use in the treatment or prevention of disease caused by *S. pneumoniae* and/or *Haemophilus influenzae* infection A further aspect of the invention is use of the immunogenic composition or vaccine or kit of the invention in the manufacture of a medicament for the treatment or prevention of bacterial diseases. A further aspect of the invention is use of the immunogenic composition or vaccine or kit of the invention in the manufacture of a medicament for the treatment or prevention of diseases caused by *S. pneumoniae* and/or *Haemophilus influenzae* infection.

The invention also provides an activated bacterial saccharide, wherein the activated bacterial saccharide comprises a repeat unit of formula (I):

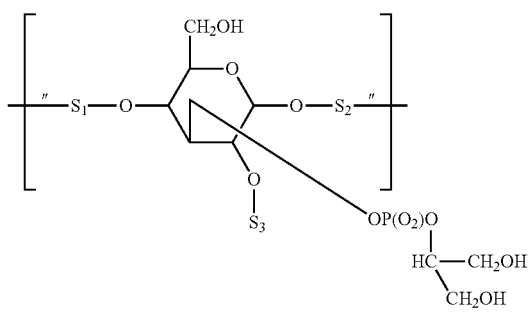

wherein the activated bacterial saccharide comprises n repeat units and n is between 2 and 2400, between 20 and 2000, between 50 and 1500, between 1000 and 2000, between 1000 and 2500 or between 1500 and 2300.

wherein at least 0.001%, 0.01%, 0.1%, 0.5%, 1%, 2%, 5%, 10% or 30% but less than 0.001%, 0.01%, 0.1%, 0.5%, 1%, 2%, 5%, 10%, 30% or 50% of S1 is

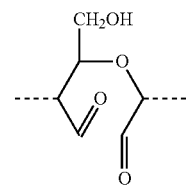

and the remainder is

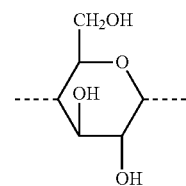

wherein S2 is either

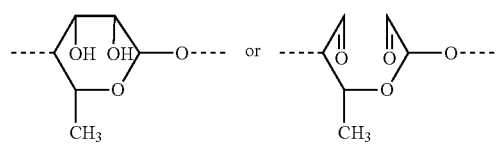

and wherein S3 is either

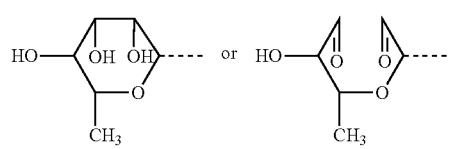

In an embodiment less than 0.001%, 0.1%, 0.5% 1%, 2%, 3%, 5%, 10%, 30% or 50% of S2 is

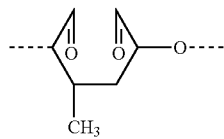

In an embodiment less than 0.1%, 0.5%, 1%, 2%, 3%, 5%, 10%, 30% or 50% of S3 is

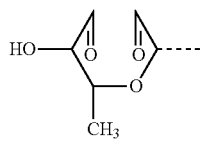

"Around" or "approximately" are defined as within 10% more or less of the given figure for the purposes of the invention.

The terms "comprising", "comprise" and "comprises" herein are intended by the inventors to be optionally substitutable with the terms "consisting of", "consist of" and "consists of", respectively, in every instance.

Embodiments herein relating to "vaccine compositions" of the invention are also applicable to embodiments relating to "immunogenic compositions" of the invention, and vice versa.

All references or patent applications cited within this patent specification are incorporated by reference herein.

In order that this invention may be better understood, the following examples are set forth. These examples are for purposes of illustration only, and are not to be construed as limiting the scope of the invention in any manner.

EXAMPLES

Example 1

Oxidation of 23F and 6B Using Periodate

Polysaccharides (PS) 23F or 6B were dissolved in 100 mM $KH_2PO_4$ (pH 7.4), 10 mM $KH_2PO_4$ or WFI, to form solutions of 2 mg PS/ml. The solution was incubated for 2 hours under agitation at room temperature. After this time the pH was adjusted to pH 6.0 with 1 NHCl. Periodate was added as a powder or in liquid form (10 mg/ml in WFI) in various amounts to achieve a range of molar ratios (table 1). The solutions were incubated for 17 hours at room temperature (20-25° C.), after which time the samples were dialyzed or diafiltered against WFI.

High performance gel filtration chromatography coupled with refractive index and multiangle laser lights scattering (MALLS-) detectors was used to measure the molecular weight. Size exclusion media (TSK5000PWXL-Tosoh) was used to profile the molecular size distribution of the polysaccharide (elution 0.5ml/min in NaCl 0.2M-NaN3 0.02%).

Table 1 and FIG. 1 describe the results of these experiments. These demonstrate that for the 23F saccharide substantial sizing occurs on oxidation using high molar equivalents of periodate in 100 mM phosphate buffer. This sizing effect can be reduced by reducing the concentration of phosphate buffer or the molar equivalents of periodate used.

TABLE 1

| | 23F | | | | 6B | | |
|---|---|---|---|---|---|---|---|
| Sample | molar equivalent of periodate | Buffer | Size (KDa) | Sample | molar equivalent of periodate | buffer | Size (KDa) |
| 23F native | 0 | Water | 861 | 6B | 0 | 10 mM phosphate | 1022 |
| 23F native | 0 | 10 mM phosphate | 847 | 6B | 0.1 | 10 mM phosphate | 975 |
| 23F native | 0 | 100 mM phosphate | 860 | 6B | 0.2 | 10 mM phosphate | 990 |
| 23F ATCC native | 0 | 100 mM phosphate | 1655 | 6B | 0.3 | 10 mM phosphate | 961 |
| 23F | 1 | 100 mM phosphate | <1 | 6B | 0.75 | 10 mM phosphate | 868 |
| 23F | 1 | Water | 36 | | | | |
| 23F | 1.2 | 100 mM phosphate | <1 | | | | |
| 23-FATCC | 1 | 100 mM phosphate | 2 | | | | |
| 23-FATCC | 0.125 | 100 mM phosphate | 39 | | | | |
| 23F | 0.1 | 10 mM phosphate | 466.9 | | | | |
| 23F | 0.15 | 10 mM phosphate | 398.5 | | | | |
| 23F | 0.2 | 10 mM phosphate | 336 | | | | |
| 23F | 0.5 | 10 mM phosphate | 179.1 | | | | |

Example 2

Conjugation of 23F to CRM197 Using Reductive Amination and CDAP Chemistry

Reductive Amination 1 g of PS23F was dissolved in 500 ml of 10 mM $KH_2PO_4$, pH 7.15. This solution was incubated at room temperature for two hours. The pH was adjusted to 6.0N with 1M HCl. 111 mg of periodate ($NaIO_4$, 0.4 molar equivalents of periodate) was added to the PS23F solution, and the solution was incubated for 17 hours in the dark at room temperature to oxidise PS23F. The solution was then diafiltered against WFI.

The activated PS23F was lyophilised with the CRM197 protein (at a CRM/PS ratio (w/w): 0.625) in the presence of a stabilising agent.

900 mg of the lyophilised PS23F/CRM197 mixture was solubilised by addition of 350 ml of DMSO solvent and incubating for 2 hours at room temperature. To reduce the PS23F/CRM197 mixture 1 molar equivalent of $NaBH_3CN$ was added (735 µl of a solution of 100 mg/ml in WFI). The solution was incubated for a further 40 hours room temperature (15° C.-25° C.) under agitation. After this time 2 molar equivalent of $NaBH_4$ (100 mg/ml in WFI) was added and the solution incubated for 4 hours at room temperature. 2200 ml of 150 mM NaCl was added before diafiltration (cut-off 100 kDa) and purification by DEAE. The fractions of interest were pooled and filtered through a 0.22 µm filter.

CDAP 200 mg of microfluidized PS23F was dissolved in water until a concentration of 10 mg/ml was obtained. NaCl was added to this solution at a final concentration of 2M.

Sufficient CDAP solution (100 mg/ml freshly prepared in 5/50 v/v acetonitrile/WFI) was added to reach a CDAP:PS ratio of 0.75 mg/mg PS.

After 90 seconds, the pH was raised to pH 9.5 by addition of 0.1 N NaOH.

3 minutes later sufficient CRM197 (10 mg/ml in 0.15M NaCl) was added to reach a ratio of 1.5 (CRM197:PS (w/w)), the pH was maintained at pH 9.5. This solution was incubated for 1 hour at pH 9.5.

After this coupling step, 10 ml of 2M glycine solution was added to the mixture and the pH was adjusted to pH9.0 (the quenching pH). The solution was stirred for 30 minutes at room temperature. The conjugate was purified using a 5 µm filter followed by Sephacryl S400HR (XK50/100) which removes small molecules and unconjugated polysaccharides and protein. The flow rate was fixed at 150 ml/hour. Elution was achieved using 150 mM NaCl. The fractions of interest were pooled and filtered using Milipack 20. The resulting conjugate had a final CRM197/PS ratio (w/w) of 1.35/w.

Example 3

Immunogenicity of 23F-CRM197 Conjugates Made by Reductive Amination and CDAP Chemistry Conjugates were made using the methods described in example 2. Female guinea pigs were immunized intramuscularly three times (at days 0, 14 and 28) with 0.25 µg of the PS23F-CRM197 conjugates. Animals were bled on day 42 and the antibody response directed against PS23F was measured by ELISA and OPA.

ELISA

Microplates were coated with purified pneumococcal polysaccharide in PBS buffer. The plates were washed four times with 0.9% NaCl and 0.05% Tween 20. Sera were incubated for 1 hour at 37° C. with CPS (V/V) in PBS 0.05% Tween 20. Sera were added to the microwells and serially diluted (two-fold dilution step) in PBS-0.05% Tween. The plates were incubated under agitation for 30 minutes at room temperature. The plates were washed as above and an anti-guinea pig IgG antibodies peroxydase conjugate was added, the plates were then incubated for 30 minutes at RT. After washing, the substrate (4 mg of OPDA in 10 ml of citrate 0.1M pH 4.5 and 5 µl of $H_2O_2$) was added to each well for 15 minutes. The reaction was stopped by addition of HCl 1N. Absorbance was read at 490-620 nm using a spectrophotometer. The colour developed is directly proportional to the amount of antibody present in the serum. The level of anti-PS IgG present in the sera is determined by comparison to the reference curve serum added on each plate and expressed in µg/ml.

Results were analysed statistically after assuming homogeneity of variance (checked by Cochrans's C test) and normality (checked using the Shapiro-Wilk test). All statistics were carried out using Anova (Tukey-HSD) on log transformation concentration IgG.

Opsonophagocytosis

Serum samples were heated for 45 min at 56° C. to inactivate any remaining endogenous complement. Twenty-five microlitre aliquots of each 1:2 diluted serum sample were serially diluted (two fold) in 25 µl OPA buffer (HBSS—14.4% inactivated FBS) per well of a 96-well round bottom microtitre plate. Subsequently, 25 µl of a mixture of activated HL-60 cells ($1 \times 10^7$ cells/ml), freshly thawed pneumococcal working seed and freshly thawed baby rabbit complement in an e.g. 4/2/1 ratio (v/v/v) was added to the diluted sera to yield a final volume of 50 µl. The assay plate was incubated for 2 h at 37° C. with orbital shaking (210 rpm) to promote the phagocytic process. The reaction was stopped by laying the microplate on ice for at least 1 min. A 20 µl aliquot of each well of the plate was then transferred into the corresponding well of a 96-well flat bottom microplate and 50 µl of Todd-Hewitt Broth-0.9% agar was added to each well. After overnight incubation at 37° C. and 5% CO2, pneumococcal colonies appearing in the agar were counted using an automated image analysis system (KS 400, Zeiss, Oberkochen, Germany). Eight wells without serum sample were used as bacterial controls to determine the number of pneumococci per well. The mean number of CFU of the control wells was determined and used for the calculation of the killing activity for each serum sample. The OPA titre for the serum samples was determined by the reciprocal dilution of serum able to facilitate 50% killing of the pneumococci. The opsonophagocytic titre was calculated by using a 4-parameter curve fit analysis.

Results were analysed statistically after assuming homogeneity of variance (checked by Cochrans's C test) and normality (checked using the Shapiro-Wilk test). All statistics were performed by Anova (Tukey-HSD) on log transformation concentration IgG for ELISA and Kruskal-Wallis on log dilution for OPA.

A significantly higher antibody response was induced in the guinea pigs after immunisation with PS23F-CRM197 conjugated by reductive amination than PS23F-CRM197 conjugated by CDAP chemistry as seen in FIG. 2.

TABLE 2

| Assay | 23F-CRM197 made by reductive amination | 23F-CRM197 made by CDAP |
|---|---|---|
| ELISA liter (µ/ml) | 213.3 | 40.5 |
| OPA (50% killing) | 9232 | 591 |

Example 4

A Further Example of Reductive Amination of 23F

23F-CRM-RA-116

150 mg of native PS23F (PS23FP114) was dissolved at a concentration of 2 mg/ml in 10 mM phosphate buffer (pH 7.2) for 4 hours. After dissolution, pH was adjusted to pH 6.0 with 1N HCl. Then 0.4 molar equivalent of periodate (Na $IO_4$) was added to the PS solution and incubated for 17 hrs in the dark at 25° C. The solution is then diafiltered (cut off 30 kDa) against WFI and the oxidised PS was filtered on 0.22 µm membrane.

50 mg of oxidised PS and 75 mg of CRM197 were lyophilized together (CRM/PS ratio (w/w): 1.5/1) in the presence of a stabilising agent. Lyophilized PS+CRM197 was solubilised with 20 ml of DMSO for 2 hrs at room temperature (15-25° C.). 1 molar equivalent of TAB (Sodium triacetoxyborohydride) was then added (13.7 mg) and after 17 hrs under agitation, 2 molar equivalent of $NaBH_4$ (100 mg/ml in 0.1M NaOH) was added followed by an incubation at room temperature for 30 minutes. The solution was diluted 5× by addition of WFI followed by a diafiltration (cut-off 30 kDa) against 10 mM phosphate buffer, 150 mM NaCl pH 7.2. The conjugate was then loaded onto DEAE resin and eluted in 10 mM phosphate buffer, 500 mM NaCl pH 7.2. The conjugate was finally filtered on 0.22 μm. The resulting conjugate has a final CRM/PS ratio (w/w) of 2.3/1.

For further conjugates, a second diafiltration step was added after DEAE column in order to change the buffer (150 mM NaCl as final buffer).

Example 5

Conjugation of 6B to CRM197 Using Reductive Amination (with Different Protein:Saccharide Ratios and Different Sized Microfluidised 6B Saccharides) and CDAP Chemistry

6B-CRM-RA-122

200 mg of microfluidized PS6B (84 kDa, 11.7 mg/ml) was diluted at 2 mg/ml in 10 mM phosphate buffer (pH 7.2). pH was adjusted to pH 6.0 with 1N HCl. Then 0.1 molar equivalent of periodate (Na $IO_4$) was added to the PS solution and incubated for 17 hrs in the dark at room temperature. The solution is then diafiltered (cut off 30 kDa) against WFI. 50 mg of PS and 30 mg of CRM197 were lyophilized together (CRM/PS ratio (w/w): 0.6/1) in the presence of a stabilising agent. Lyophilized PS+CRM197 were solubilised with 20 ml of DMSO for 3 hrs at room temperature. Then 2.5 molar equivalent of TAB (Sodium triacetoxyborohydride) was added (38.7 mg) and after 16 hrs under agitation, 2 molar equivalent of $NaBH_4$ (100 mg/ml in 0.1M NaOH) was added followed by an incubation at room temperature for 30 minutes. The solution was diluted 4× by addition of WFI followed by a diafiltration (cut-off 100 kDa). The conjugate was then filtered on 0.22 μm. The resulting conjugate has a final CRM/PS ratio (w/w) of 1.1/1.

6B-CRM-RA-123:

Microfluidized PS6B (84 kDa) was conjugated to CRM197 as described for 6B-CRM-RA-122 except the freeze-drying step was carried out using an initial CRM197/PS ratio (w/w) of 2/1 and 30 ml of DMSO was used for the dissolution in DMSO step (instead of 20 ml). The resulting conjugate had a final CRM/PS ratio (w/w) of 3.0/1.

6B-CRM-RA-124:

200 mg of microfluidized PS6B (350 kDa, 11.7 mg/ml) having a molecular weight of 350 kDa was diluted to 2 mg/ml in 10 mM phosphate buffer (pH 7.2). pH was adjusted to pH 6.0 with 1N HCl. Then 0.1 molar equivalent of periodate (Na $IO_4$) was added to the PS solution and incubated for 17 hrs in the dark at room temperature. The solution is then diafiltered (cut off 100 kDa) against WFI. 50 mg of PS and 60 mg of CRM197 were lyophilized together (CRM/PS ratio (w/w): 1.2/1) in the presence of a stabilising agent. Lyophilized PS+CRM197 were solubilised with 20 ml of DMSO for 5 hrs at room temperature. 2.5 molar equivalent of TAB (Sodium triacetoxyborohydride) was then added (38.7 mg) and after 16 hrs under agitation, 2 molar equivalent of NaBH4 (100 mg/ml in 0.1M NaOH) were added followed by incubation for 30 min at room temperature. The solution was diluted 4× by addition of WFI followed by a diafiltration (cut-off 100 kDa). The conjugate was then filtered on 0.22 μm. The resulting conjugate has a final CRM/PS ratio (w/w) of 1.6/1.

6B-CRM-RA-125:

Microfluidized PS6B (350 kDa) was conjugated to CRM197 as described for 6B-CRM-RA-124 except the freeze-drying step was carried out using an initial CRM197/PS ratio (w/w) of 2/1 and the dissolution in DMSO was carried out using 33 ml (instead of 20 ml). The resulting conjugate had a final CRM/PS ratio (w/w) of 2.9/1.

6B-CRM-003:

50 mg of microfluidized PS6B were diluted at 10 mg/ml in water (10 mg/ml). NaCl in solid form was added to reach a final concentration of 2M. CDAP solution (100 mg/ml freshly prepared in 50/50 v/v acetonitrile/WFI) was added to reach the appropriate CDAP/PS ratio (1.5 mg/mg PS). After 1.5 minutes, the pH was raised to the activation pH 9.5 by addition of 0.1N NaOH and was stabilised at this pH until addition of CRM197. After 3 minutes, CRM197 (10 mg/ml in 0.15 M NaCl) was added to reach a ratio CRM197/PS (w/w) of 2; the pH was maintained at the coupling pH 9.5. The solution was left for 2 hrs under pH regulation.

After the coupling step, 2.5 ml of 2M glycine solution was added to the mixture. The pH was adjusted to the quenching pH (pH 9.0). The solution was stirred for 30 min at room temperature. Then the conjugate was filtered using a 5 μm filter and injected on Sephacryl S400HR (XK26/100) column to remove small molecules (including DMAP) and unconjugated PS and protein. Flow rate was fixed at 30 ml/h. Elution was carried out in 150 mM NaCl. Interesting fractions were pooled and filtered on Millipack 20. The resulting conjugate had a final CRM197/PS ratio (w/w) of 1.5/1.

6B-CRM-RA-144

1 g of microfluidized PS6B (245 kDa, 9.47 mg/ml) was diluted to 2 mg/ml in 10 mM phosphate buffer (pH 7.2). The pH was adjusted to pH 6.0 with 1N HCl. 0.1 molar equivalent of periodate ($NaIO_4$) was then added to the PS solution and incubated for 18 hrs in the dark at room temperature. The solution was then diafiltered against WFI (Sartocon Slice200 Hydrosart 100 kDa). 200 mg of oxidized PS and 240 mg of CRM197 were lyophilized together (CRM/PS ratio (w/w): 1.2/1) in the presence of a stabilising agent. Lyophilized PS+CRM197 were solubilised with 80 ml of DMSO for 6 hrs at 25° C. Then 2.5 molar equivalent of TAB (Sodium triacetoxyborohydride) was added (154.9 mg) and after 16 hrs under agitation at 25° C., 2 molar equivalent of $NaBH_4$(100 mg/ml in 0.1M NaOH) was added and incubated for 30 min. The solution was diluted 5× in WFI and after 30 min was diafiltered 10× with 150 mM NaCl and then 5× with $PO_4$ ($K/K_2$) 10 mM pH7.2+150 mM NaCl (Sartorius Sartocon Slice 200 Hydrosart 100 kDa). Then the retentate was loaded onto a DEAE column (XK26/40). The column was washed with $PO_4$ ($K/K_2$) 10 mM pH7.2/NaCl 150 mM buffer. The conjugate was eluted with $PO_4$ ($K/K_2$) 10 mM pH7.2/NaCl 500 mM buffer. The eluate was concentrated and diafiltered with 5 volumes of 150 mM NaCl and then filtered on 0.22 μm filter. The resulting conjugate has a final CRM/PS ratio (w/w) of 1.6/1.

Example 6

Immunogenicity of 6B-CRM197 Conjugates Made by Reductive Amination and CDAP Chemistry Groups of 40 female Balb/c mice (4 weeks-old) were immunized intramuscularly three times at days 0, 14 and 28 with 0.1 μg of PS6B conjugates produced by reductive amination or CDAP chemistry formulated on $AlPO_4$. PS6B-PD was used as benchmark. Mice were bled on day 42 and the antibody response directed against each antigen was measured by ELISA and OPA.

Groups of 20 female guinea pig (150 gr from Hartley) were immunized intramuscularly three times at days 0, 14 and 28 with 0.25 μg of PS6B conjugates produced by reductive amination or CDAP chemistry adjuvanted with AlPO$_4$. PS6B-PD was used as benchmark. Guinea pigs were bled on day 42 and the antibody response directed against each antigen was measured by ELISA and OPA.

Mouse and Guinea Pig OPA

Serum samples were heated for 45 min at 56° C. to inactivate any remaining endogenous complement. Twenty-five microlitre aliquots of each 1:2 diluted serum sample was two-fold serially diluted in 25 μl OPA buffer (HBSS—14.4% inactivated FBS) per well of a 96-well round bottom microtitre plate. Subsequently, 25 μl of a mixture of activated HL-60 cells (1×10$^7$ cells/ml), freshly thawed pneumococcal working seed and freshly thawed baby rabbit complement in an e.g. 4/2/1 ratio (v/v/v) were added to the diluted sera to yield a final volume of 50 μl. The assay plate was incubated for 2 h at 37° C. with orbital shaking (210 rpm) to promote the phagocytic process. The reaction was stopped by laying the microplate on ice for at least 1 min. A 20 μl aliquot of each well of the plate was then transferred into the corresponding well of a 96-well flat bottom microplate and 50 μl of Todd-Hewitt Broth-0.9% agar was added to each well. After overnight incubation at 37° C. and 5% CO$_2$, pneumococcal colonies appearing in the agar were counted using an automated image analysis system (KS 400, Zeiss, Oberkochen, Germany). Eight wells without serum sample were used as bacterial controls to determine the number of pneumococci per well. The mean number of CFU of the control wells was determined and used for the calculation of the killing activity for each serum sample. The OPA titre for the serum samples was determined by the reciprocal dilution of serum able to facilitate 50% killing of the pneumococci. The opsonophagocytic titre was calculated by using a 4-parameter curve fit analysis. Table 3 Describes the GMC Levels Obtained by Immunisation of Balb/C Mice with the Conjugates Made Using the Methods of Example 4.

Figure 4:
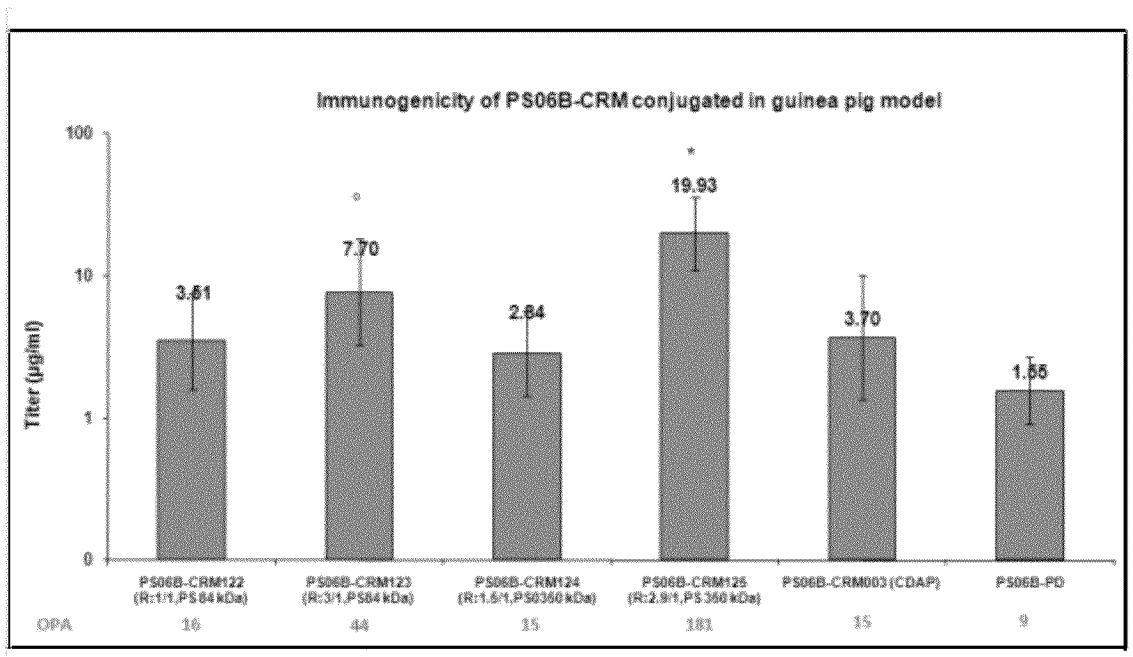
FIG. 4 Evaluation of the immunogenicity of PS06B-CRM conjugated using the conjugation methods described in example 4 in a guinea pig model.

The immunogenicity of these conjugates in guinea pigs is described in FIG. 4. Similar to the experiments carried out in the mouse model, the results in table 4 and FIG. 4 show that the conjugates produced by reductive amination are comparable with those produced using CDAP chemistry, in particular PS06B-CRM125 demonstrated significantly higher GMC levels and immunogenicities than the conjugate produced using CDAP.

Example 7

Conjugation of Hib to Tetanus Toxoid Using Reductive Amination

Hib-IO4-LS080

2.9 g of PS (orcinol dosage, AHIBCPA007 lot) were dissolved in 260 ml of 10 mM phosphate buffer (Na/K$_2$) pH 6.2 for 4 h30 at room temperature and then overnight at +4° C. The viscosity follow-up was done during the dissolution. After 4 hours dissolution the viscosity seemed to be stable. PS was diluted at 10 mg/ml with phosphate buffer and then oxidised in the dark with 0.07 molar equivalent of NaIO$_4$ during 60 minutes. Oxidised PS was diafiltered (Sartorius Hydrosart 2 kDa) against 3.5 volumes of phosphate buffer and then filtered on a 0.22 μm filter. The number of repeating units obtained after oxidation was estimated by $^1$H-NMR and was found to be around 21.

Hib-TT-LS210, 212 and 213

200 mg of oxidised PS (14.56 mg/ml) were mixed with 300 mg of TT (31.18 mg/ml, TT/PS ratio (w/w): 1.5/1) and diluted to 4 mg/ml with 36.64 ml of 10 mM phosphate buffer (Na/K$_2$) pH 6.2. The solution was lyophilized in the presence of a stabilising agent. Lyophilized PS+TT was solubilised with 20 ml of DMSO for 6 hrs at 25° C. Then 10 Meq of TAB (Sodium

TABLE 3

| | G1 | G2 | G3 | G4 | G5 | G6 |
|---|---|---|---|---|---|---|
| Subject/Result | PS06B-CRM122 (R: 1/1, PS 84 kDa) | PS06B-CRM123 (R: 3/1, PS 84 kDa) | PS06B-CRM124 (R: 1.5/1, PS 350 kDa) | PS06B-CRM125 (R: 2.9/1, PS 350 kDa) | PS06B-CRM003 (CDAP) | PS06B-PD |
| GMC (UG-ML) | 0.83 | 0.37 | 1.18 | 0.64 | 0.31 | 0.10 |
| Responders (%) | 31/40 | 26/40 | 33/40 | 29/40 | 29/40 | 15/40 |

Figure 3:
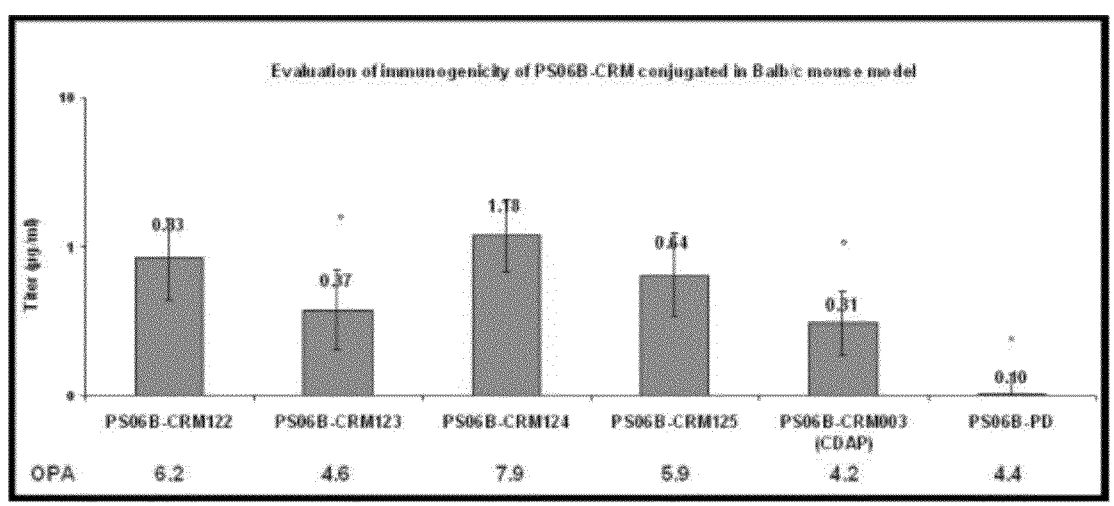
FIG. 3 Evaluation of the immunogenicity of PS06B-CRM conjugated using the conjugation methods described in example 4 in a Balb/c mouse model.

The immunogenicity of these conjugates in balb/c mice is described in FIG. 3. Together FIG. 3, and table 3 demonstrate that in the mouse model the conjugates produced by reductive amination were comparable with those produced using CDAP chemistry. In particular FIG. 3 demonstrates that the immunogenicities of the conjugates produced using reductive amination was higher than the immunogenicity of the conjugate made using CDAP chemistry.

Table 4 describes the GMC levels obtained by immunisation of guinea pigs with the conjugates made using the methods of example 4.

triacetoxyborohydride) were added (38.7 mg) and after 16 hrs under agitation, 2 molar equivalent of NaBH$_4$ (100 mg/ml in 0.1M NaOH) was added followed by an incubation for 30 min at room temperature. The solution was diluted 3× by addition of WFI followed by a diafiltration step (5 volumes of WFI followed by 5 volumes of 10 mM acetate buffer 150 mM NaCl pH 6.2, 100 kDa MWCO). The sample was then loaded on Sephacryl S300HR resin. Elution was carried out in 10 mM acetate buffer using 150 mM NaCl (pH 6.2). Interesting fractions were pooled and filtered on a 0.22 μm filter. The resulting conjugates had a final TT/PS ratio (w/w) of 2.1/1.

TABLE 4

| | G1 | G2 | G3 | G4 | G5 | G6 |
|---|---|---|---|---|---|---|
| Subject/Result | PS06B-CRM 122 (R: 1/1, PS 84 kDa) | PS06B-CRM123 (R: 3/1, PS84 kDa) | PS06B-CRM124 (R: 1.5/1, PS0350 kDa) | PS06B-CRM125 (R: 2.9/1, PS 350 kDa) | PS06B-CRM003 (CDAP) | PS06B-PD |
| GMC (UG-ML) | 3.51 | 7.70 | 2.84 | 19.93 | 3.70 | 1.55 |
| Responders (%) | 20/20 | 20/20 | 20/20 | 20/20 | 20/20 | 20/20 |

The invention claimed is

1. A process for conjugating a bacterial saccharide and reducing the sizing effect on bacterial saccharide comprising the steps of
   a) reacting the bacterial saccharide with 0.001-0.7 molar equivalents of periodate to form an activated bacterial saccharide,
   b) mixing the activated bacterial saccharide with a carrier protein;
   c) reacting the activated bacterial saccharide and the carrier protein with a reducing agent to form a conjugate;
   wherein step a) occurs in a buffer which does not contain an amine group, and the buffer has a concentration between 1-100 mM and wherein the bacterial saccharide is S.pneumoniae capsular saccharide 23F.

2. The process of claim 1 wherein the buffer is selected from the group consisting of phosphate buffer, borate buffer, acetate buffer, carbonate buffer and citrate buffer.

3. The process of claim 1 wherein the pH in step a) is pH 3.5-8.0.

4. The process of claim 1 wherein the average molecular weight of the bacterial saccharide is between 1-1100 kDa after step a).

5. The process of claim 1 wherein the average molecular weight of the 23F saccharide is between 100-470 kDa after step a).

6. The process of claim 1 wherein the carrier protein is selected from the group consisting of tetanus toxoid, fragment C of tetanus toxoid, diphtheria toxoid, CRM197, Pneumolysin, protein D, PhtD, PhtDE and N19.

7. The process of claim 1 wherein the reducing agent comprises sodium cyanoborohydride or sodium triacetoxyborohydride.

8. The process of claim 1 comprising a further step e) of purifying the conjugate.

9. The process of claim 1 containing a further step of mixing the conjugate with further antigens.

10. The process of claim 9 wherein the further antigens comprise one or more S.pneumoniae proteins selected from the group consisting of the Poly Histidine Triad family (PhtX), Choline Binding Protein family (CbpX), CbpX truncates, LytX family, LytX truncates, CbpX truncate-LytX truncate chimeric proteins (or fusions), pneumolysin (Ply), PspA, PsaA, Sp128, Sp101, Sp130, Sp125 and Sp133.

11. The process of claim 1 wherein the conjugate is mixed with an adjuvant or a pharmaceutically acceptable excipient.

* * * * *